United States Patent
Xue et al.

(10) Patent No.: US 12,217,144 B2
(45) Date of Patent: Feb. 4, 2025

(54) MACHINE-LEARNED STATE SPACE MODEL FOR JOINT FORECASTING

(71) Applicant: Google LLC, Mountain View, CA (US)

(72) Inventors: Yuan Xue, Palo Alto, CA (US); Dengyong Zhou, Redmond, WA (US); Nan Du, San Jose, CA (US); Andrew Mingbo Dai, San Francisco, CA (US); Zhen Xu, Sunnyvale, CA (US); Kun Zhang, Pleasanton, CA (US); Yingwei Cui, Palo Alto, CA (US)

(73) Assignee: GOOGLE LLC, Mountain View, CA (US)

( * ) Notice: Subject to any disclaimer, the term of this patent is extended or adjusted under 35 U.S.C. 154(b) by 1193 days.

(21) Appl. No.: 17/008,338

(22) Filed: Aug. 31, 2020

(65) Prior Publication Data

US 2021/0065066 A1 Mar. 4, 2021

Related U.S. Application Data

(60) Provisional application No. 62/893,837, filed on Aug. 30, 2019.

(51) Int. Cl.
*G06N 20/20* (2019.01)
*G06F 17/16* (2006.01)
*G06F 17/18* (2006.01)
*G06N 3/02* (2006.01)

(52) U.S. Cl.
CPC ............ *G06N 20/20* (2019.01); *G06F 17/16* (2013.01); *G06F 17/18* (2013.01); *G06N 3/02* (2013.01)

(58) Field of Classification Search
CPC .......... G06N 20/20; G06N 3/02; G06F 17/16; G06F 17/18
See application file for complete search history.

(56) References Cited

U.S. PATENT DOCUMENTS

2013/0116999 A1* 5/2013 Stein ...................... G16H 50/50
703/11
2020/0005941 A1* 1/2020 Saria ...................... G16H 50/20

OTHER PUBLICATIONS

Gewitz, Andrew, "A sequential Monte Carlo Approach to Joint Longitudinal and Time-to-Event Modeling," dissertation, Stanford University (2015) (Year: 2015).*
Welch et al., "An Introduction to the Kalman Filter" (2016), archived Jan. 27, 2018, retrieved on Jun. 1, 2024 from https://web.archive.org/web/20180127081820/https://www.cs.unc.edu/~welch/media/pdf/kalman_intro.pdf (Year: 2018).*

(Continued)

*Primary Examiner* — Miranda M Huang
*Assistant Examiner* — Yao David Huang
(74) *Attorney, Agent, or Firm* — DORITY & MANNING P.A.

(57) ABSTRACT

A deep state space generative model is augmented with intervention prediction. The state space model provides a principled way to capture the interactions among observations, interventions, critical event occurrences, true states, and associated uncertainty. The state space model can include a discrete-time hazard rate model that provides flexible fitting of general survival time distributions. The state space model can output a joint prediction of event risk, observation and intervention trajectories based on patterns in temporal progressions, and correlations between past measurements and interventions.

20 Claims, 6 Drawing Sheets

(56) References Cited

OTHER PUBLICATIONS

Rolfe, Jason, "Discrete Variational Autoencoders," arXiv:1609.02200v2 [stat. ML] Apr. 22, 2017 (Year: 2017).*
Berchuck et al., "Scalable Modeling of Spatiotemporal Data Using the Variational Autoencoder: An Application in Galucoma," arXiv:1908.09195v1 [stat.AP] Aug. 24, 2019 (Year: 2019).*
Luo, Ya, "Joint Modeling of Longitudinal and Survival Data via Multivariate Mixed Effects State Space Model," dissertation, University of California Santa Barbara (2018) (Year: 2018).*
Doerr et al., "Probabilistic Recurrent State-Space Models," Proceedings of the 35 th International Conference on Machine Learning, Stockholm, Sweden, PMLR 80, 2018 (Year: 2018).*
Abadi et al, "TensorFlow: Large-Scale Machine Learning to Heterogeneous Systems", arXiv:1603v2, Mar. 16, 2016, 19 pages.
Alaa et al, "Deep Multi-Task Gaussian Processes for Survival Analysis with Competing Risks", Advances in Neural Information Processing Systems, 2017, 9 pages.
Barretta et al, "Gaussian Process Regression for Survival Data with Competing Risks", arXiv:1312v2, Sep. 5, 2014, 36 pages.
Chapfuwa et al, "Adversarial Time-to-Event Modeling", arXiv:1804v2, Jun. 7, 2018, 14 pages.
Che et al, "Recurrent Neural Networks for Multivariate Time Series with Missing Values", arXiv:1606v2, Nov. 7, 2016, 14 pages.
Choi et al, "Doctor AI: Predicting Clinical Events via Recurrent Neural Networks", arXiv:1511v11, Sep. 28, 2016, 18 pages.
Cox, "Regression Models and Life-Tables", Journal of the Royal Statistical Society, Series B, vol. 34, No. 2, 1972, pp. 187-220.
Elhadad et al, "Deep Survival Analysis", arXiv:1608v2, Sep. 18, 2016, 13 pages.
Fernandez et al, "Gaussian Processes for Survival Analysis", arXiv:1611v1, Nov. 2, 2016, 13 pages.
Fraccaro et al, "A Disentangled Recognition and Nonlinear Dynamics Model for Unsupervised Learning", arXiv:1710v2, Oct. 30, 2017, 13 pages.
Fraccaro et al, "Sequential Neural Models with Stochastic Layers", arXiv:1605v2, Nov. 13, 2016, 10 pages.
Ghassemi et al, "Predicting Intervention Onset in the ICU with Switching State Space Models", Summits on Translational Science Proceedings, 2017, 10 pages.
Giunchiglia et al, "RNN-SURV: A Deep Recurrent Model for Survival Analysis", Conference on Artificial Neural Networks, 2018, 10 pages.
Haarnoja et al, "Backprop KF: Learning Discriminative Deterministic State Estimators", arXiv:1605v4, Oct. 1, 2017, 11 pages.
Johnson et al, "MIMIC III, A Freely Accessible Critical Care Database", Scientific Data, 2016, 9 pages.
Kalman, "A New Approach to Linear Filtering and Prediction Problems", Journal of Basic Engineering, 1960, pp. 35-45.
Karl et al, "Deep Variational Bayes Filters: Unsupervised Learning of State Space Models from Raw Data", arXiv:1605v3, Mar. 3, 2017, 13 pages.
Krishnan et al, "Deep Kalman Filters", arXiv:1511v2, Nov. 25, 2015, 17 pages.
Krishnan et al, "Structured Inference Networks for Nonlinear State Space Models", arXiv:1609v2, Dec. 5, 2016, 13 pages.
Lee et al, "Deephit: A Deep Learning Approach to Survival Analysis with Competing Risks", Association for the Advancement of Artificial Intelligence, 2018, 8 pages.
Lipton et al, "Learning to Diagnose with LSTM Recurrent Neural Networks", arXiv:1511v7, Mar. 21, 2017, 18 pages.
Liu et al, "Clinical Time Series Prediction with a Hierarchical Dynamical System", Artificial Intelligence in Medicine, 2013, 11 pages.
Liu et al, "Learning Adaptive Forecasting Models from Irregularly Sampled Multivariate Clinical Data", Artificial Intelligence, 2016, 16 pages.
Mei et al, "The Neural Hawkes Process: A neutrally Self-Modulating Multivariate Point Process", Advances in Neural Information Processing Systems, 2017, 11 pages.
Raghu et al, "Continuous State-Space Models for Optimal Sepsis Treatment: A Deep Reinforcement Learning Approach", arXiv:1705v1, May 23, 2017, 17 pages.
Rajkomar et al, "Scalable and Accurate Deep Learning with Electronic Health Records", Digital Medicine, 2018, 10 pages.
Rangapuram et al, "Deep State Space Models for Time Series Forecasting", Advances in Neural Information Processing Systems, 2018, 10 pages.
Sha et al, "Interpretable Predictions of Clinical Outcomes with an Attention-Based Recurrent Neural Network", Conference on Bioinformantics, Computational Biology and Health Information, Aug. 2017, 16 pages.
Song et al, "Attend and Diagnose: Clinical Time Series Analysis using Attention Models", arXiv:1711v2, Nov. 19, 2017, 8 pages.
Wu et al, "Understanding Vasopressor Intervention and Weaning: Risk Prediction in a Public Heterogeneous Clinical Time Series Database", Journal of the American Medical Informatics Association, 2016, pp. 488-495.
Ye et al, "A Multi-Task Learning Formulation for Survival Analysis", Conference on Knowledge Discovery and Data Mining, 2016, 10 pages.
Zheng et al, "Deep Recurrent Survival Analysis", arXiv:1809v2, Nov. 13, 2018, 8 pages.
Zhou et al, "Multi-Task Survival Analysis", Conference on Data Mining, 2017, 11 pages.

* cited by examiner

MACHINE-LEARNED STATE SPACE MODEL FOR JOINT FORECASTING

CROSS-REFERENCE TO RELATED APPLICATIONS

This application claims priority to and the benefit of U.S. Provisional Patent Application No. 62/893,837 filed on Aug. 30, 2019, which is hereby incorporated by reference in its entirety.

FIELD

The present disclosure relates generally to systems and methods for joint prediction. More particularly, the present disclosure relates to systems and methods that include or employ a machine-learned state space model capable of jointly predicting a trajectory of future observations, a trajectory of future interventions, and/or a time-to-event prediction.

BACKGROUND

Various systems have benefitted from using machine-learned models for prediction such as, for instance, providing an indication of an event that is liable to happen and/or an estimation of when the event will happen. By studying these predictions, it can thus be possible to influence the event. As another example, machine-learned models can generate predicted values in a time series based on trends in the existing time series, for example, by fitting a mathematical model to the data. These predicted values can closely approximate the actual data that will be recorded in the time series.

As one example, the wide adoption of electronic medical records (EMR) has resulted in the collection of clinical measurements over time in the form of time-series data. These retrospective data contain information that captures the intricate relationships among patient conditions and outcomes and present a promising avenue for improving patient healthcare. Recently, machine learning methods have been increasingly applied to EMR data to predict patient condition as well as events, such as mortality, co-morbidity, etc. The integration of the prediction results into clinicians' workflows still faces significant challenges as the alerts generated by these machine learning algorithms can fail to provide insights into why the predictions are made and how to act on the predictions.

SUMMARY

Aspects and advantages of embodiments of the present disclosure will be set forth in part in the following description, or can be learned from the description, or can be learned through practice of the embodiments.

One example aspect of the present disclosure is directed to a machine-learned state space model capable of providing simultaneous prediction of physiological states and intervention suggestions. Specifically, the machine-learned state space model can output a joint prediction of mortality risk, observation and intervention trajectories based on patterns in temporal progressions, and correlations between past measurements and clinical interventions.

Another example aspect of the present disclosure is directed to a computer-implemented method of training a machine-learned state space model. Specifically, the method can include receiving an input time series comprising a plurality of observations. Additionally, the method can include inferring, based at least in part on the input time series, one or more latent state variables, Additionally, the method can include inferring, based at least in part on an encoder, a plurality of interventions. Additionally, the method can include generating, based at least in part on one or more generative parameters of the machine-learned state space model, a forecast associated with the input time series. Additionally, the method can include estimating a loss associated with the forecast. Additionally, the method can include updating, based at least in part on the loss, the one or more generative parameters of the machine-learned state space model.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF DRAWINGS

Detailed discussion of embodiments directed to one of ordinary skill in the art is set forth in the specification, which makes reference to the appended figures, in which.

Figure 1A:
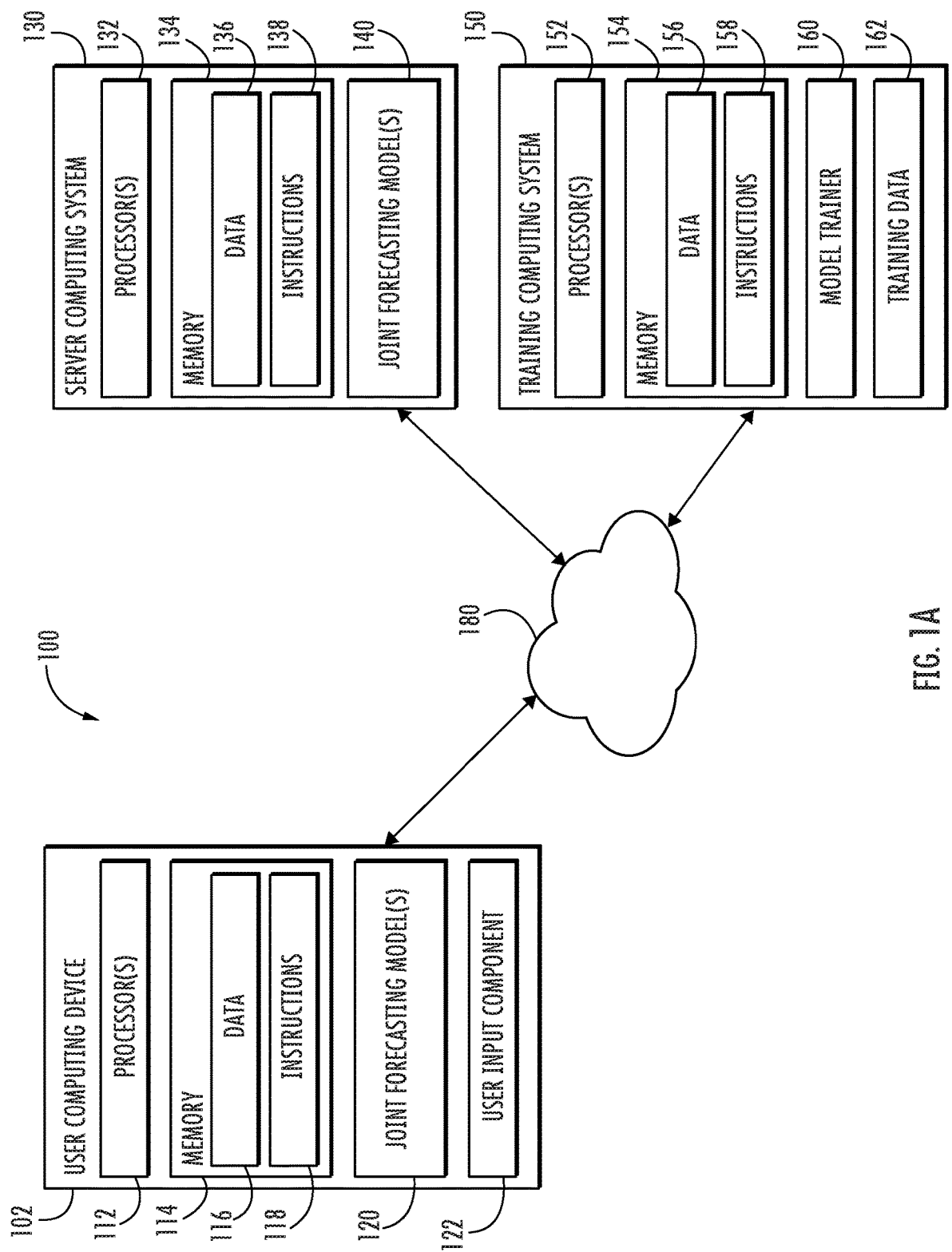
FIG. 1A depicts a block diagram of an example computing system that performs joint prediction according to example embodiments of the present disclosure.

Reference numerals that are repeated across plural figures are intended to identify the same features in various implementations.

DETAILED DESCRIPTION

Overview

Generally, the present disclosure is directed to systems and methods that train, include, and/or employ a machine-learned state space generative model capable of jointly predicting a trajectory of future observations, a trajectory of future interventions, and/or a time-to-event prediction for a system. In particular, one example application of the proposed model is to jointly forecast clinical observations, clinical interventions, and/or time to clinical event associated with a particular medical patient. However, many other systems can be modeled by the proposed state space model.

The state space model provides a principled way to capture the interactions among observations, interventions, critical event occurrences (e.g., mortality event occurrences, clinical disease onset, etc.), underlying or latent system states (e.g., physiological states), and associated uncertainty. Thus, based on the shared states (e.g., physiological states), the model is able to not only predict the trajectories of future observations and interventions, but also conduct relevant risk analysis (e.g., mortality risk). In particular, in some implementations, the state space model can include a discrete-time hazard rate model that provides flexible fitting of time-to-event distributions (e.g., general survival time distributions). For example, the hazard rate model can be a non-parametric formulation for flexible time-to-event analysis.

The proposed approach provides a number of benefits. As one example, jointly predicting multiple clinical variables can provide medical professionals with a more complete picture of patients' medical condition, thereby enabling medical professionals to make more informed decisions with regard to patient healthcare. Moreover, by illustrating the correlation between forecasted variables and mortality risk, medical professionals can be provided with evidence to more easily understand the predictions. For instance, the joint time-series trajectory and time-to-event prediction provide medical professionals with an interpretation of the occurrences of critical events by giving references to related measurements and interventions. However, it should be understood that this trajectory and time-to-event prediction are not intended to substitute for medical expertise and proper medical treatment, and are intended to serve to provide an estimation as a tool for qualified medical personnel to make informed decisions.

As another example, by predicting a future time series of the hazard function, one technical effect is to more accurately model the evolution of the survival function over a forecast horizon. For instance, in some cases such as clinical prediction, the real-world interventions can be determined in response to previous states and observations and may not be wholly external factors. By predicting a time series of the hazard function (e.g., as opposed to assuming the hazard rate is constant over all time), it is possible to model the behavior of certain real-world interventions, such as in clinical prediction. However, it should be understood that this model is not intended to substitute for medical expertise and research, and is intended to serve to provide an estimation as a tool for qualified medical personnel to make informed decisions.

Another technical effect according to the present disclosure is the capability to provide time-calibrated predictions of observations, interventions and event risk. In the case of clinical prediction, these time-calibrated predictions can also be referred to collectively as or presented in the format of a physiological state compass. The physiological state compass can give a holistic view of a patient's physiological condition over the forecast horizon by considering a more accurate model of a latent physiological condition based on several interrelated components. The physiological state compass can also serve to convey the relationship between observations, interventions, and mortality risk better than separate, unrelated models. An example physiological state compass is discussed in reference to FIG. 3.

Another technical effect according to the present disclosure can be reduced memory usage and/or faster processing time associated with the use of a single joint prediction model. For instance, systems and methods according to the present disclosure can be capable of providing a joint prediction of observations, interventions, and event risk from a single model. By using a single model, memory usage is reduced and predictions are provided faster compared to multiple separate models providing separate time series and forecast predictions. For instance, each of the multiple models can require a separate training step and prediction step, which can contribute significantly to processing time and memory usage.

Example State Space Models

As described above, one example application of the present disclosure is to jointly forecast clinical observations, clinical interventions, and/or time to clinical event associated with a particular medical patient. While this example application will now be discussed in greater detail to assist in demonstrating example aspects of the present disclosure, the proposed techniques can be applied to jointly model and predict interventions, observations, and/or time-to-event analysis for any system, including, as examples, sensors, manufacturing systems, computing systems (e.g., server clusters), mechanical systems (e.g., autonomous vehicles, driver assist systems), user interactions, chemical or biological reactions/interactions, and/or recommendation systems.

More particularly, a longitudinal EMR system can have data associated with a plurality of patients, such as N patients. Each patient i of the N patients can have records within a time window $[1, T_i]$. For instance, time 1 can represent a time when the patient first interacts with the system, such as the start of an inpatient encounter. For instance, time $T_i$ can represent a time when the patient last interacts with the system, such as the end of an impatient encounter. $T_i$ is also referred to as censor time and can vary for different patients i. The prediction given by the machine-learned state space model can optionally be personalized for each patient i. For the purpose of clarity, $T_i$ is used interchangeably herein with T.

The data used by the state space models (e.g., for training and/or inference) can be de-identified data. For example, personally identifiable information, such as location, name, exact birth date, contact information, biometric information, facial photographs, etc. can be scrubbed from the records prior to being transmitted to and/or utilized by the state space models and/or a computing system including the state space models. For example, the data can be de-identified to protect identity of individuals and to conform to regulations regarding medial data, such as HIPAA, such that no personally identifiable information (e.g., protected health information) is present in the data used by the state space models and/or used to train the state space models.

Further to the descriptions above, a user may be provided with controls allowing the user to make an election as to both if and when systems, programs, or features described herein may enable collection of user information (e.g., observations, interventions, states, etc.). In addition, certain data may be treated in one or more ways before it is stored or used, so that personally identifiable information is removed. For example, a user's identity may be treated so that no personally identifiable information can be determined for the user. Thus, the user may have control over what information is collected about the user, how that information is used, and what information is provided to the user.

For instance, a patient may be provided with controls allowing the patient to consent to collection of the patient's EMR data. As another example, the patient may be provided with controls allowing the patient to restrict some or all forms of EMR data from being collected or stored. As another example, the patient may be provided with controls allowing the patient to limit the use or continued use of the EMR data, such as by restricting the EMR data from being used as training data or for a prediction associated with a different patient. For instance, the machine-learned model can be trained using only publicly available datasets of scrubbed and de-identified data (e.g., using no data derived from patients).

Inputs to the machine-learned state space model can include time-series data. For instance, the time-series data can be EMR data, such as EMR data for a particular patient and/or for a plurality of patients. For instance, the time-series data can be defined over a time window, such as the time window $[1, T_i]$. In some embodiments, the inputs can be normalized. For instance, the inputs can be normalized using z-score, where the mean and standard deviation of each feature are computed based on training data.

For instance, the time-series data can include a plurality of observations. For the purpose of illustration, the plurality of observations is represented mathematically as a vector x. The vector x can be real-valued. The vector x can have O dimensions. For instance, each dimension can correspond to a different type or modality of observation. The vector x can be represented over a time series. For the purposes of illustration, $x_{1:T}$ is used to mathematically denote the sequence of observations at discrete time points $t=1, \ldots, T$; For instance, $x_{1:T}$ can be a matrix, such as an O by T matrix.

In some embodiments, each dimension in each observation can correspond to a type of clinical measurement. Example clinical measurements include vital signs and lab results, such as mean blood pressure, serum lactate, length of stay, survival data, diagnostic codes, and other suitable clinical measurements. For instance, the clinical measurements can be measured in a clinic, hospital, or other suitable location. The clinical measurements can be associated with a patient. In some embodiments, the clinical measurements are defined and/or measured at each of the discrete time points.

In some cases, the clinical measurements can have one or more irregular values (e.g., missing values) resulting from, for instance, irregular measurement intervals, data loss or corruption, inaccurate readings, inability to measure, or any other suitable reason. In some embodiments, irregular values can be inferred from other values, such as by using a value of the same type of clinical measurement occurring in the time-series data before or after an irregular value in place of the irregular value. Any suitable method of inferring missing values can be used in accordance with the present disclosure.

Additionally and/or alternatively, the time-series data can include a plurality of interventions. For the purpose of illustration, the plurality of interventions is represented mathematically as a vector u, The vector u can be real-valued. The vector u can have I dimensions. For instance, each dimension can correspond to a different type or modality of intervention. The vector u can be represented over a time series. For the purposes of illustration, $u_{1:T}$ is used to mathematically denote the sequence of interventions at discrete time points $t=1, \ldots, T$; For instance, $u_{1:T}$ can be a matrix, such as an 1 by T matrix.

In some embodiments, each intervention in the plurality of interventions can correspond to a measured intervention at a point in time. Each intervention can have one or more dimensions, each dimension corresponding to a type of intervention, such as a type of clinical intervention. Example clinical interventions include administering of medication, usage of a mechanical ventilator, procedure codes, dialysis, or other suitable clinical interventions. Values of these clinical interventions may include, for example, an amount of medication, settings of a mechanical ventilator, procedure code, settings of a dialysis machine, or other suitable values.

In some cases, the plurality of interventions can have one or more missing values. In some cases, it is not known if the missing values are a result of an incomplete intervention or an intervention that was otherwise not performed or an intervention continued from the previous value with no change. One example method for guessing the reason for the missing value is to derive the distribution of inter-medication-administration time and the inter-intervention-setting time. As one example, a 90-percentile time can be used as the cut-off threshold. If two consecutive interventions are within the time range of their corresponding thresholds, then the missing value can be considered as an indication of a continuous action and the last value of the intervention is used in place of the missing value. If it falls outside of this range, then a missing value can be considered as no action.

The point in time in the time-series data at which the machine-learned state space model begins its prediction is referred to as prediction time, denoted by $t^*$. The sequence of observations and interventions up to this time is referred to as $x_{1:t^*}$, $u_{1:t^*}$. For instance, $x_{1:t^*}$, $u_{1:t^*}$ can represent a sequence of time-series data from when a patient begins an inpatient encounter to the time at which the time-series data is no longer available or otherwise chosen for input into the model, such as the moment the model is used. The observations and interventions can include no personally-identifiable information, such as protected health information.

Based on the time-series data before prediction time, the state space model can predict one or more trajectory predictions of the time-series data. For example, a trajectory forecast can include a future time series of future observations associated with the plurality of observations. Alternatively or additionally to the predicted future observations, a trajectory forecast can include a future time series of future interventions associated with the plurality of interventions. Thus, in some implementations, a future time series of observations and interventions can be jointly predicted, mathematically represented by $x_{t^*+\tau}$ and $u_{t^*+\tau}$ where $\tau \in [1, H]$. For example, i can represent a future time period over which the future time series is/are predicted. The future time period may represent real-life time (e.g., a magnitude of seconds, minutes, hours, days, etc.) and/or a number of data points (e.g., 10 estimated data points). This is also referred to as the forecast horizon.

In addition to the one or more trajectory predictions, the machine-learned state space model according to the present disclosure can provide a time-to-event prediction associated with the one or more trajectory predictions. The time-to-event prediction can be jointly predicted along with the one or more trajectory predictions. The time-to-event prediction is discussed herein with regard to mortality events, such as the onset of an acute condition or death. However, the systems and methods disclosed herein can easily be extended to other events.

An event can be represented as a tuple $(c, t^e)$. For instance, $t^e$ can denote the time to the event from the prediction time $t^*$. For instance, c can be representative of censorship. Censorship can be an indication if the event is observed or expected to be observed before the end of the time-series data. In other words, if an event is not censored, the event occurs sometime in the time window $[1, T]$. For instance, if the event is observed, then $t^e <= T$ and $c=0$. However, if the event is censored then $t^e = T$ and $c=1$.

Time-to-event prediction can be performed by analyzing a survival function defined as $S(t)=Pr(t^e \geq t)$. The survival function can be a monotonically decreasing function representing the probability of $t^e$ not occurring earlier than t. The survival function is related to a hazard function which is defined mathematically as $\lambda(t)$. The hazard function represents the rate of an event occurring at time t given that no event occurred before time t. In other words, $\lambda(t)$ can be used to determine S(t) which can better capture the risk of a patient experiencing event e at t. In accordance with the present disclosure, the machine-learned state space model can be configured to predict a future time series of the hazard function over the forecast horizon [t*+1, t*+τ] where τ∈[1, H].

For instance, the future time series of the hazard function can be predicted jointly with the one or more trajectory predictions. By predicting the future time series of the hazard function, one technical effect is to more accurately model the evolution of the survival function over the forecast horizon [t*+1, t*+τ]. For instance, in some cases such as clinical prediction, the real-world interventions can be determined (e.g., by a medical professional) in response to previous states and observations and may not be wholly external factors. By predicting a time series of the hazard function (e.g., as opposed to assuming the hazard rate is constant over all time), it is possible to model the behavior of certain real-world interventions, such as in clinical prediction, by modeling the dependency between real-world observations and real-world interventions.

Another technical effect according to the present disclosure is the capability to provide time-calibrated predictions of observations, interventions and event risk. In the case of clinical prediction, these time-calibrated predictions are referred to collectively as the physiological state compass. The physiological state compass can give a holistic view of a patient's physiological condition over the forecast horizon by considering a more accurate model of a latent physiological condition based on several interrelated components. The physiological state compass can also serve to convey the relationship between observations, interventions, and mortality risk better than separate, unrelated models. An example physiological state compass is discussed in reference to FIG. 3.

Figure 1B:
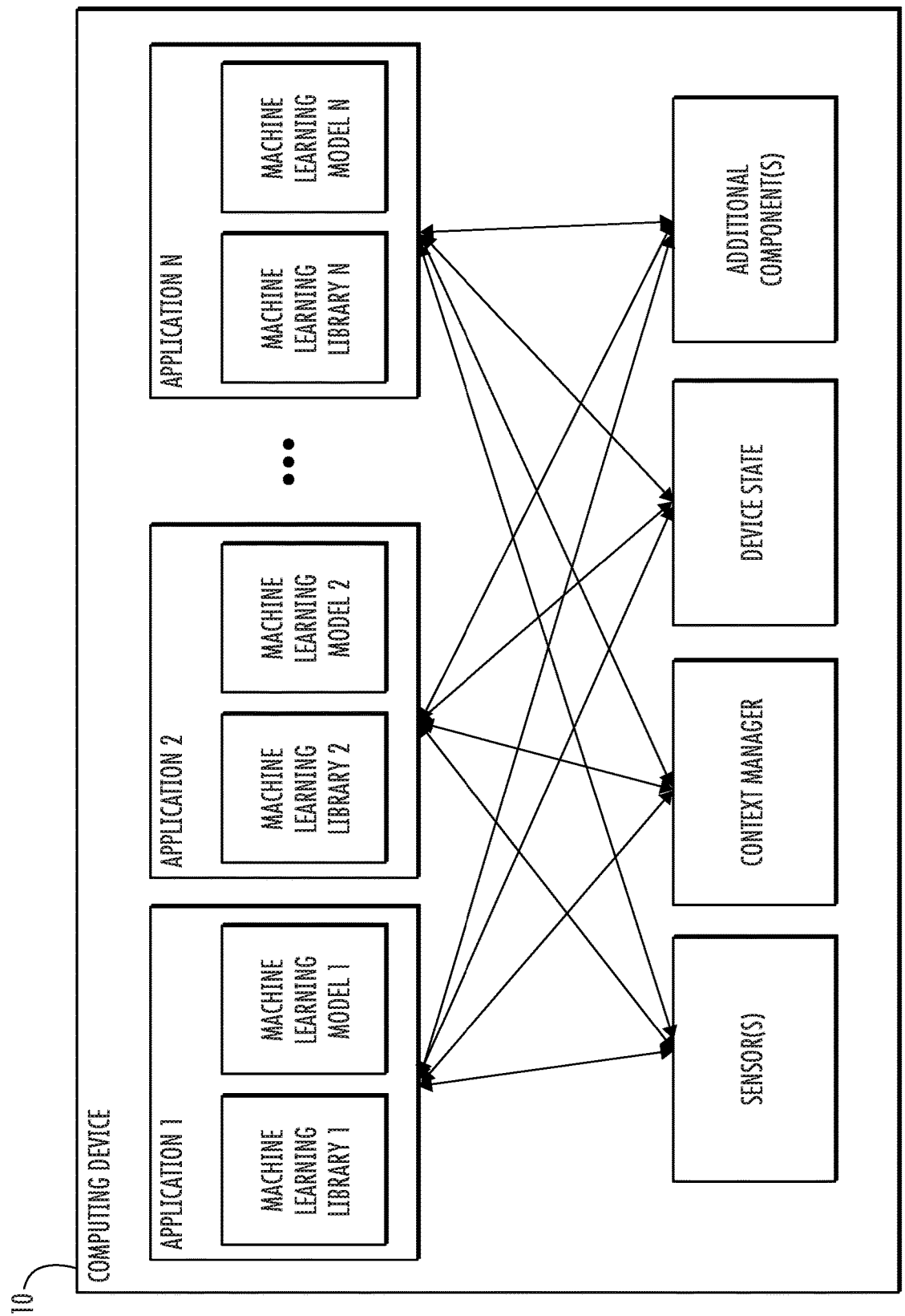
FIG. 1B depicts a block diagram of an example computing device that performs joint prediction according to example embodiments of the present disclosure.
Figure 1C:
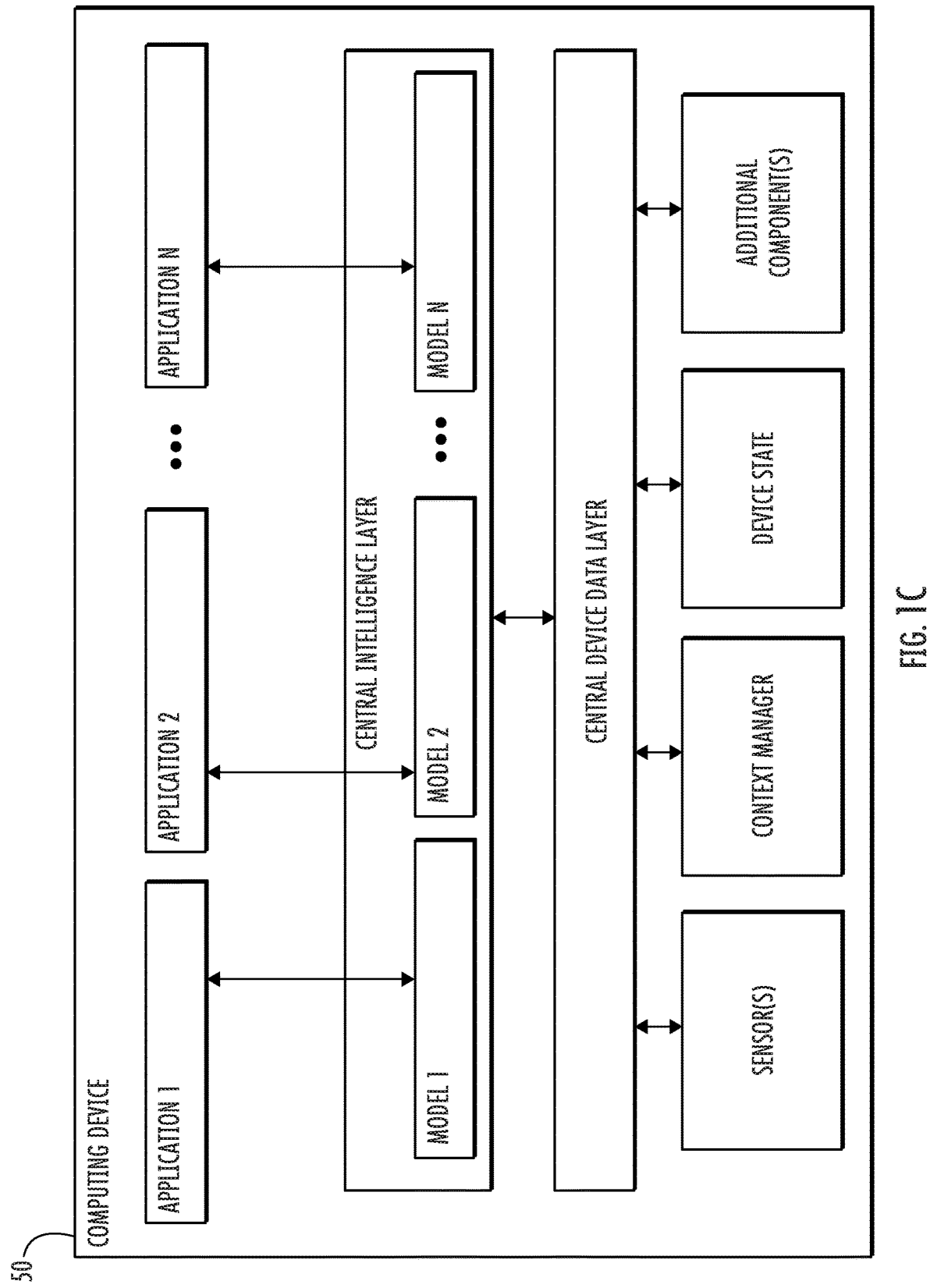
FIG. 1C depicts a block diagram of an example computing device that performs joint prediction according to example embodiments of the present disclosure.
Figure 2:
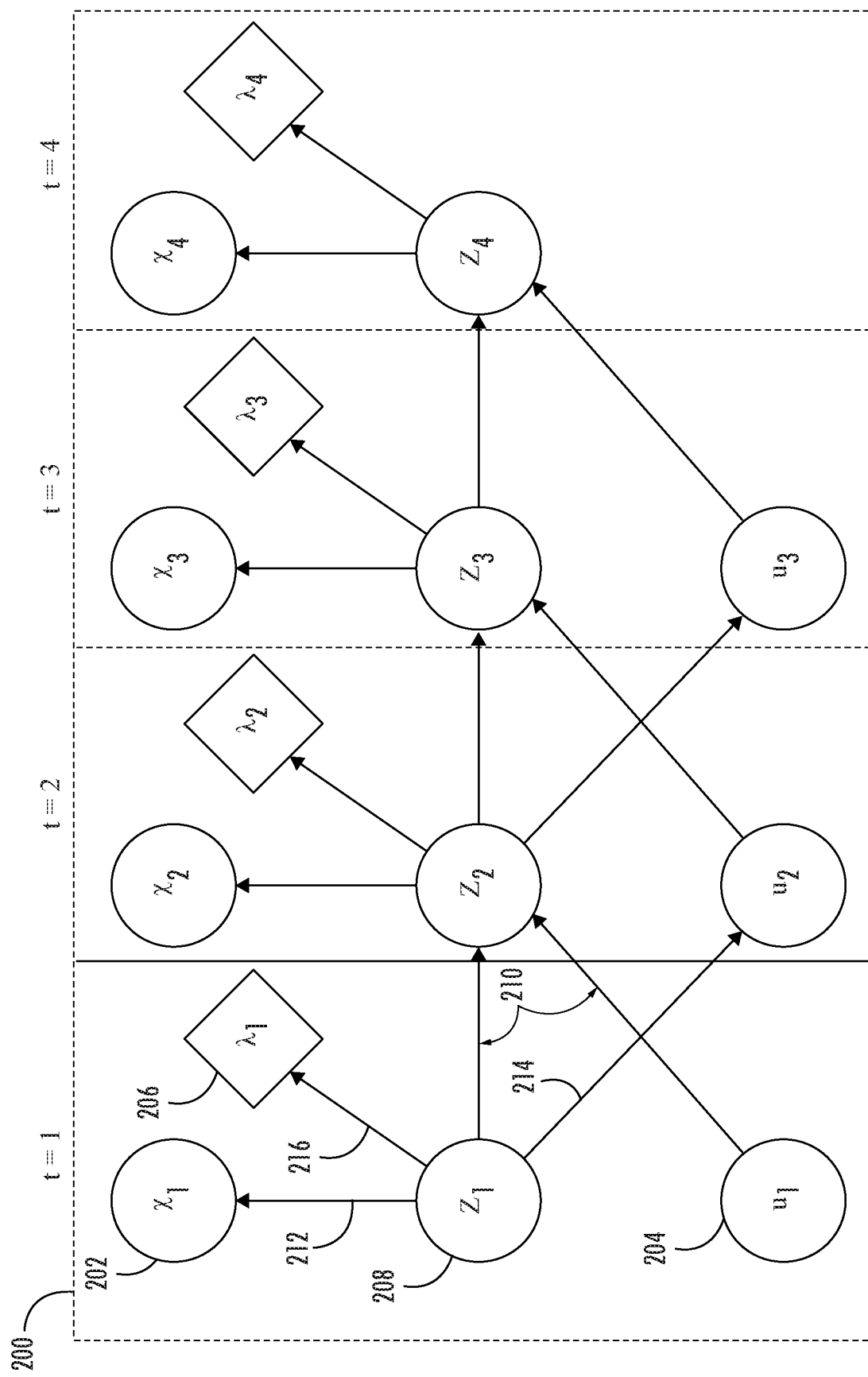
FIG. 2 depicts an example state space model according to embodiments of the present disclosure.

FIG. 2 depicts an example state space model 200 that may be employed according to example embodiments of the present disclosure. For instance, state space model 200 may be the joint prediction models 120, 140 that are discussed with reference to FIG. 1. For instance, the state space model 200 may be a Gaussian state space model.

The state space model 200 includes one or more state variables 208 (represented as $z_t$) that represent the physiological state at time t. The sequence of the one or more state variables 208 over a time window [1, T] is represented as $z_{1:T}$. The state space model 200 is illustrated with four instances t=1, . . . , 4, and as such is configured to provide the one or more future trajectories having four points. More or fewer instances may be used in accordance for the present disclosure. For example, if it was desired to predict the one or more future trajectories having ten points, a state space model with ten instances t=1, . . . , 10 may be used.

The state space model 200 defines how the one or more state variables 208 evolve from a first instance to a second instance. For instance, the one or more state variables 208 at a first instance and a second instance can be related by transition equation 210. For example, transition equation 210 may be defined as:

$$p(z_t|z_{t-1}, u_t) \sim \mathcal{N}(\mathcal{A}_t(z_{t-1}) + \mathcal{B}_t(u_t), Q)$$

where $\mathcal{A}$ is a function that defines how the system transitions without external influence (i.e., how state variables 208 will evolve from $z_{t-1}$ to $z_t$ without interventions 204) and $\mathcal{B}$ captures the effect of interventions 204 ($u_{t-1}$) on state variables 208 ($z_t$). In some embodiments, $\mathcal{A}$ and $\mathcal{B}$ can be matrices, such as matrices whose values are determined using machine-learning. In some embodiments, $\mathcal{A}$ and $\mathcal{B}$ can be parameterized by one or more neural networks, such as neural networks trained on combinations of state variables 208 at a previous instance ($z_{t-1}$) and/or state variables 208 at a current instance ($z_t$). Q is a process and measurement noise covariance matrix. In some embodiments, Q is assumed to be time invariant. For instance, in some embodiments, Q can be initialized as a unit variable.

At each instance, the state space model 200 is configured to output one or more observations 202. The one or more observations 202 are related to the one or more state variables 208 at the same point in time by an emission equation 212. For instance, the emission equation may be defined as:

$$p(x_t|z_t) \sim \mathcal{N}(C(z_t), R)$$

where C is a function relating state variables 208 ($z_t$) and observations 202 ($x_t$). For instance, in some embodiments, C can be a matrix, such as a matrix whose values are determined using machine-learning. In some embodiments, C can be parameterized by a neural network, such as a neural network trained on combinations of state variables 208 ($z_t$) and/or observations 202 ($x_t$). R is a process and measurement noise covariance matrix. In some embodiments, R is assumed to be time invariant. For instance, in some embodiments R can be initialized as a unit variable.

The combination of the transmission equation 210 and emission equation 212 subsumes a large family of linear and non-linear Gaussian state space models. For example, by setting $\mathcal{A}$, $\mathcal{B}$, C to be matrices, the state space model 200 is a linear state space model. As another example, if $\mathcal{A}$, $\mathcal{B}$, and C are parameterized via deep neural networks, the state space model 200 is a deep Gaussian state space model.

The state space model 200 includes an additional dependency 214 between the state variables 208 at $z_t$ to intervention 204 at $u_{t+1}$. This is especially useful in cases where the state space model 200 represents medical data, as the interventions are typically determined by medical professionals based on their estimation of patient states, medical knowledge, etc. As such, the effect that a present state has on a future intervention is captured as well as the effect that a present intervention has on a future state. For instance, the additional dependency 214 may be defined as:

$$p(u_t|z_{t-1}) \sim \mathcal{N}(\mathcal{D}(z_{t-1}), U)$$

where $\mathcal{D}$ is a function relating state variables 208 ($z_{t-1}$) and interventions 204 ($u_t$). For instance, in some embodiments, $\mathcal{D}$ can be a matrix, such as a matrix whose values are determined using machine-learning. In some embodiments, $\mathcal{D}$ can be parameterized by a neural network, such as a neural network trained on combinations of state variables 208 ($z_{t-1}$) and/or interventions 204 ($u_t$). U is a process and measurement noise covariance matrix. In some embodiments, U is assumed to be time invariant. For instance, in some embodiments U can be initialized as a unit variable.

In the state space model 200, the hazard rate 206 is discretized per time step and dependent on the state variables 208 at that time. For instance, the hazard rate 206 at time step t can be modeled by a hazard rate dependency 216. For example, hazard rate dependency 216 may be defined as:

$$\lambda_t = \mathcal{L}(z_t)$$

where $\mathcal{L}$ is a function relating state variables 208 ($z_t$) and hazard rate 206 ($\lambda_t$). For instance, in some embodiments, $\mathcal{L}$ can be a matrix, such as a matrix whose values are determined using machine-learning. In some embodiments, $\mathcal{L}$ can be parameterized by a neural network, such as a neural network trained on combinations of state variables 208 ($z_{t-1}$) and/or hazard rate 206 ($\lambda_t$).

Based on the hazard rate 206, it is possible to determine a survival function associated with the hazard rate 206. For example, one survival function at time t can be defined as:

$$S(t)=(1-\lambda_t)S(t-1).$$

Let $S(0)=1$. The above recursion leads to:

$$S(t)=\Pi_{s=1}^{t}(1-\lambda_S).$$

The incidence density function is defined as $f_t=Pr(t^e=t)$ and is connected with $\lambda_t$ via $$f(t)=\lambda_t \Pi_{s=1}^{t-1}(1-\lambda_S).$$

The state space model 200 thus can be specified by the generative parameter $\theta=(\mathcal{A}, \mathcal{B}, \mathcal{C}, \mathcal{D}, \mathcal{L})$. One method to estimate these parameters (e.g., by training) can be referred to as system identification. An example method of system identification is to maximize the data likelihood in the entire patient record (or multiple patient records). For instance, a joint likelihood of observations and interventions can be maximized. For example, the joint likelihood of observations and interventions can be maximized according to the following equation:

$$\log p_\theta(x_{1:T}, u_{2:T}) = \log \int_z p_\theta(x_{1:T}, u_{2:T}, z_{1:T})$$

This log likelihood can be intractable when inferring the posterior $p_\theta(z_{1:T}|x_{1:T}, u_{2:T})$. One proposed method to overcome this is a variational inference method performed by introducing a variational distribution $q_\phi$ that approximates the posterior. For instance, the variational distribution may be introduced by an encoder. To simply the notations, $u_1$ is assumed to be a fixed zero vector and x is used for $x_{1:T}$, u is used for $u_{1:T}$, and z is used for $z_{1:T}$. The evidence lower bound (ELBO) is optimized as follows:

$$\log p_\theta(x, u) \geq$$

$$\mathbb{E}_{q_\phi(z|x,u)}[\log p_\theta(x|z)] + \mathbb{E}_{q_\phi(z|x,u)}[\log p_\theta(u|z)] - \mathbb{KL}(q_\phi(z|x, u) \| p_\theta(z|x, u))$$

This ELBO can be factorized along time as:

$$\sum_{t=1}^{T} \mathbb{E}_{q_\phi(z_t|x,u)}[\log p_\theta(x_t|z_t)] + \sum_{t=1}^{T-1} \mathbb{E}_{q_\phi(z_t|x,u)}[\log p_\theta(u_{t+1}|z_t)] -$$

$$\sum_{t=2}^{T} \mathbb{KL}(q_\phi(z_t|z_{t-1}, x, u) \| p_\theta(z_t|z_{t-1}, u_{t-1}))$$

The ELBO in the above equation includes a reconstruction loss for both observation and intervention and a regularization loss which measures the difference between the variational distribution $q_\phi$ and the simple prior distribution $p_\theta$ of the state z given the transition equation. For instance, in the above equation the regularization loss is represented by a Kullback-Leibler divergence between the variational distribution and the prior distribution. By choosing $\theta$ that minimizes the ELBO, the joint likelihood of observations and interventions is accordingly maximized. For instance, $\theta$ may be determined by gradient descent of the ELBO.

In some implementations, the state space model can be configured to output the one or more trajectory predictions by maximizing the joint likelihood of observation and intervention in the forecast horizon $[t^*+1, t^*+\tau]$ given their historical values within time range $[1, t^*]$. In some embodiments, reconstructing the observations and interventions in the dataset for each patient, such as described by system identification, may contribute to predicting their values over the forecast horizon $[t^*+1, t^*+\tau]$ if the system dynamics are homogeneous. The joint likelihood, the corresponding ELBO and its time-factorized form are provided below. To simply the notations, $\vec{x}, \vec{u}$ are used to represent the forecast value $\vec{x}_{t^*+1:t^*+\tau}, \vec{u}_{t^*+1:t^*+\tau}$, $\bar{x}, \bar{u}$ are used to represent the historical values $\bar{x}_{1:t^*}, \bar{u}_{1:t^*}$, and $\tilde{z}$ is used to represent $z_{1:t^*+\tau}$, the state connecting the historical values to the forecast horizon.

$$\log p_\theta(\vec{x}, \vec{u}|x, u) = \log \int_z p_\theta(\vec{x}, \vec{u}, z|x, u) =$$

$$\log \int_z p_\theta(z|x, u)p_\theta(\vec{x}|z)p_\theta(\vec{u}|z) \geq \mathbb{E}_{q_\phi(z|x,u)}[\log p_\theta(\vec{x}|z)] +$$

$$\mathbb{E}_{q_\phi(z|x,u)}[\log p_\theta(\vec{u}|z)] - \mathbb{KL}(q_\phi(z|x, u) \| p_\theta(z|x, u)) =$$

$$\sum_{t=t^*+1}^{t^*+\tau} \mathbb{E}_{q_\phi(z_t|x,u)}[\log p_\theta(x_t|z_t)] + \sum_{t=t^*+1}^{t^*+\tau} \mathbb{E}_{q_\phi(z_t|x,u)}[\log p_\theta(u_t|z_{t-1})] -$$

$$\sum_{t=1}^{t^*+\tau} \mathbb{KL}(q_\phi(z_t|z_{t-1}, x, u) \| p_\theta(z_t|z_{t-1}, u))$$

The forecast ELBO as given by the above equation includes a forecast loss for both observations and interventions over the forecast horizon, which is represented by the third line in the above equation, and a regularization loss for state z from the history to the forecast horizon, which is represented by a Kullback-Leibler divergence.

For instance, an object of training the state space model can be to minimize the forecast ELBO in addition to and/or alternatively to minimizing the system identification ELBO. For instance, the forecast ELBO can be minimized based on the predicted forecast horizon to fine-tune the model after system identification is performed.

The state space model is capable of providing a time-to-event prediction that estimates the time distribution of event time $t^e$ at prediction time $t^*$ based on the historical values of the observations and interventions $\bar{x}, \bar{u}$ based on a log likelihood of an event happening at event time $t^e$. The log likelihood of an event happening at event time $t^e$ is given by the following equation where $\hat{z}=z_{1:t^e}$:

$$\log p_\theta(t^e|x, u) = \underbrace{(1-c) \cdot \log f_\theta(t^e|x, u)}_{\text{event is observed at } t^e} + \underbrace{c \cdot \log S_\theta(t^e|x, u)}_{e \text{ is censored/survived at } t^e} =$$

$$(1-c) \cdot \log \int_{\hat{z}} p_\theta(\hat{z}|x, u)f_\theta(t^e|\hat{z}) + c \cdot \log \int_{\hat{z}} p_\theta(\hat{z}|x, u)S_\theta(t^e|\hat{z})$$

The ELBO of the log event time likelihood is given as:

$$(1-c) \cdot \mathbb{E}_{q_\phi(\hat{z}|x,u)}[\log f_\theta(t^e|\hat{z})] + c \cdot \mathbb{E}_{q_\phi(\hat{z}|x,u)}[\log S_\theta(t^e|\hat{z})] -$$

-continued $$\mathbb{KL}(q_\phi(\hat{z} \mid \bar{x}, \bar{u}) \| p_\theta(\hat{z} \mid x, u)) q_\phi(\hat{z} \mid x, u) q_\phi(\hat{z} \mid x, u) =$$

$$(1-c) \cdot \mathop{\mathbb{E}}_{q_\phi(z_t \mid x, u)} \left[ \sum_{s=1}^{t^e-1} \log(1 - p_\theta(\lambda_t \mid z_t)) + p_\theta(\lambda_t \mid z_t) \right] +$$

$$c \cdot \left[ \sum_{s=1}^{t^e} \log(1 - p_\theta(\lambda_t \mid z_t)) \right] -$$

$$\sum_{t=1}^{t^e} \mathbb{KL}(q_\phi(z_t \mid z_{t-1}, x, u) \| p_\theta(z_t \mid z_{t-1}, u))$$

Similarly to the system identification ELBO and forecast ELBO described earlier, minimizing the time-to-event ELBO can serve to maximize the log likelihood of an event occurrence. By maximizing the log likelihood of event occurrence, the model can be adjusted to more accurately represent the forecast horizon.

The machine-learned state space model according to the present disclosure can thus be trained according to a learning algorithm. For instance, the learning algorithm includes inference of z from x. Additionally, the learning algorithm includes inference of u, such as by an encoder network $q_\phi$.

The learning algorithm can include sampling based on the current estimate of the posterior z to generate a training prediction. For example, the training prediction may include reconstructed observations and interventions (e.g., for use with the system identification task described above). As another example, the training prediction may include a forecast of one or more future observations and interventions (e.g., for trajectory prediction as described above). As another example, the training prediction may include a likelihood of an event of interest (e.g., for a time-to-event prediction). The training prediction may be based on a generative model $p_\theta$. In some cases, the generative model can output the training prediction for a plurality of time steps.

The learning algorithm can include estimating gradients of the loss (e.g., a negative ELBO) with respect to θ and/or φ. The learning algorithm can include updating parameters of the model based on the gradient of the loss. In some embodiments, gradients can be averaged across subsets of a complete training set. In some embodiments, a LSTM can be used as the encoder network and/or multi-layer perceptron networks can be used for the state transition, observation emission, and hazard rate generation functions. In some embodiments, one or more of the training predictions as described above can be used to train the model concurrently as a multi-task training framework.

Example State Compass

Figure 3:
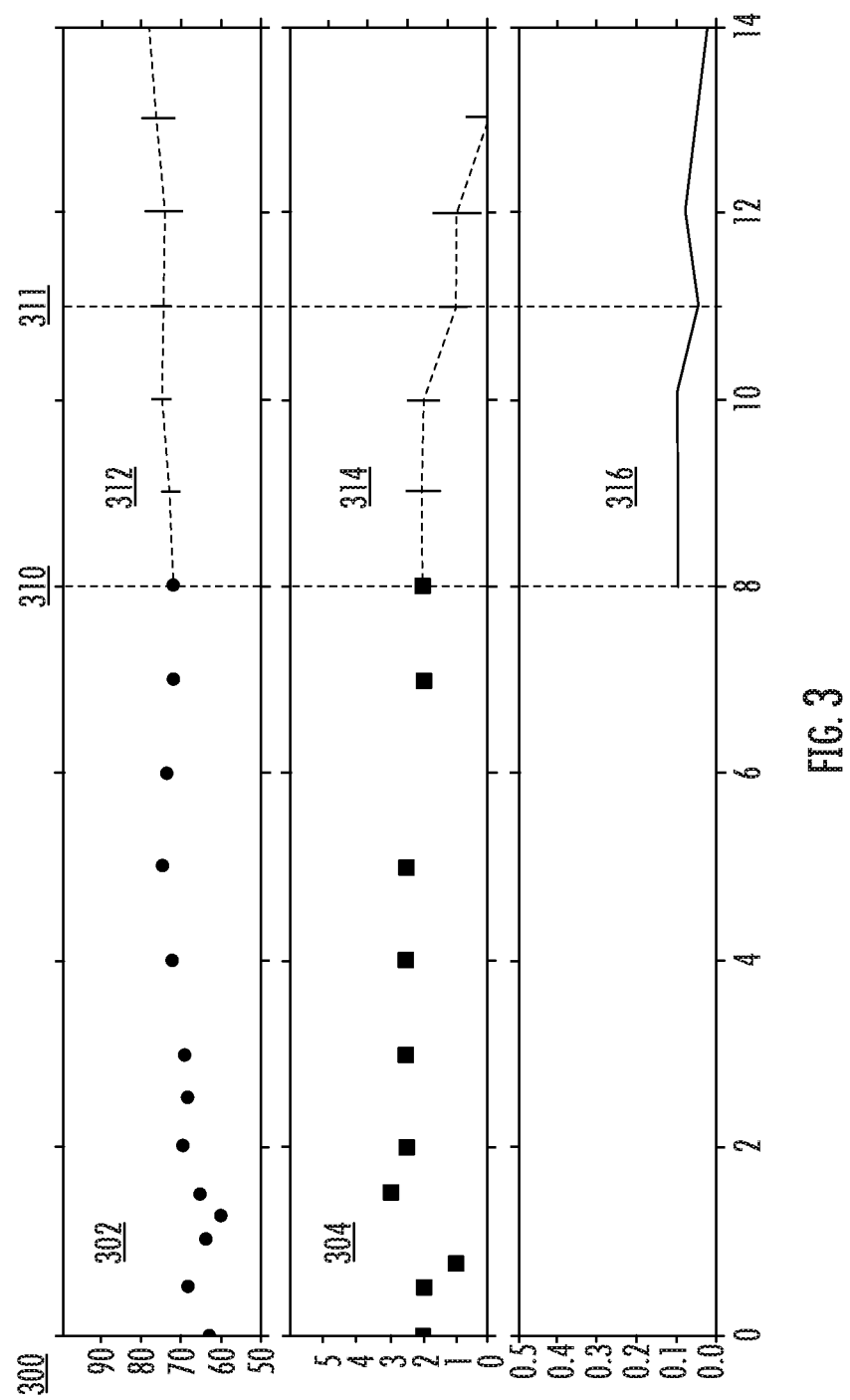
FIG. 3 depicts an example physiological state compass according to embodiments of the present disclosure.

FIG. 3 depicts an example physiological state compass 300 according to example embodiments of present disclosure. The state compass (or similar) can be presented within a user interface of a computing device.

The physiological state compass depicted in FIG. 3 illustrates a time series of observation values 302 (e.g., shown as a single dimension for purpose of clarity) and a time series of intervention values 304 (e.g., shown as a single dimension for purpose of clarity). Although a single dimension for each of the observation and intervention are illustrated, multiple observations and/or interventions (e.g., which may correspond to different dimensions) may be included in the physiological state compass in accordance with the present disclosure. As illustrated, the observation 302 and intervention 304 are captured in a time series until prediction time 310. At prediction time 310, the prediction of observation future trajectory 312 and intervention future trajectory 314 begins. Additionally, at prediction time 310, the future time series of the hazard function 316 begins.

The combination of observation future trajectory 312, intervention future trajectory 314, and future time series of the hazard function 316 can convey a correlation between them. For instance, a decrease in the hazard function 316 is illustrated at the dashed line 311. As can be seen from the intervention future trajectory 314 at dashed line 311, the drop in the hazard function 316 correlates with a decrease in the intervention future trajectory 314. Thus, it can be inferred (e.g., by a medical professional observing physiological state compass 300) that the decrease in the intervention future trajectory 314 is responsible for the decrease in the hazard function 316, and furthermore that performing a corresponding decrease in intervention 304 will decrease the chance of the event associated with the hazard rate function 316 from occurring for the patient corresponding to physiological state compass 300. In this manner, the physiological state compass is able to convey important correlations between a patient's observations, interventions, and mortality risk (e.g., to a medical professional), which can serve to advise future treatment of the patient.

Example Devices and Systems

FIG. 1A depicts a block diagram of an example computing system 100 that performs joint prediction according to example embodiments of the present disclosure. The system 100 includes a user computing device 102, a server computing system 130, and a training computing system 150 that are communicatively coupled over a network 180.

The user computing device 102 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 102 includes one or more processors 112 and a memory 114. The one or more processors 112 can be any suitable processing device (e.g., a processor core, a microprocessor, an ASIC, a FPGA, a controller, a microcontroller, etc.) and can be one processor or a plurality of processors that are operatively connected. The memory 114 can include one or more non-transitory computer-readable storage mediums, such as RAM, ROM, EEPROM, EPROM, flash memory devices, magnetic disks, etc., and combinations thereof. The memory 114 can store data 116 and instructions 118 which are executed by the processor 112 to cause the user computing device 102 to perform operations.

In some implementations, the user computing device 102 can store or include one or more joint prediction models 120. For example, the joint prediction models 120 can be or can otherwise include various machine-learned models such as neural networks (e.g., deep neural networks) or other types of machine-learned models, including non-linear models and/or linear models. Neural networks can include feed-forward neural networks, recurrent neural networks (e.g., long short-term memory recurrent neural networks), convolutional neural networks or other forms of neural networks. Example joint prediction models 120 are discussed with reference to FIG. 2.

In some implementations, the one or more joint prediction models 120 can be received from the server computing system 130 over network 180, stored in the user computing device memory 114, and then used or otherwise implemented by the one or more processors 112. In some implementations, the user computing device 102 can implement multiple parallel instances of a single joint prediction model 120 (e.g., to perform parallel joint prediction across multiple instances of clinical data).

More particularly, the joint prediction model 120 is capable of providing simultaneous prediction of physiological states and intervention suggestions. Specifically, the joint prediction model 120 can output a joint prediction of event risk, observation and intervention trajectories based on patterns in temporal progressions, and correlations between past measurements and interventions.

Additionally or alternatively, one or more joint prediction models 140 can be included in or otherwise stored and implemented by the server computing system 130 that communicates with the user computing device 102 according to a client-server relationship. For example, the joint prediction models 140 can be implemented by the server computing system 140 as a portion of a web service (e.g., a joint prediction service). Thus, one or more models 120 can be stored and implemented at the user computing device 102 and/or one or more models 140 can be stored and implemented at the server computing system 130.

The user computing device 102 can also include one or more user input component 122 that receives user input. For example, the user input component 122 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone, a traditional keyboard, or other means by which a user can provide user input.

The server computing system 130 includes one or more processors 132 and a memory 134. The one or more processors 132 can be any suitable processing device (e.g., a processor core, a microprocessor, an ASIC, a FPGA, a controller, a microcontroller, etc.) and can be one processor or a plurality of processors that are operatively connected. The memory 134 can include one or more non-transitory computer-readable storage mediums, such as RAM, ROM, EEPROM, EPROM, flash memory devices, magnetic disks, etc., and combinations thereof. The memory 134 can store data 136 and instructions 138 which are executed by the processor 132 to cause the server computing system 130 to perform operations.

In some implementations, the server computing system 130 includes or is otherwise implemented by one or more server computing devices. In instances in which the server computing system 130 includes plural server computing devices, such server computing devices can operate according to sequential computing architectures, parallel computing architectures, or some combination thereof.

As described above, the server computing system 130 can store or otherwise include one or more machine-learned joint prediction models 140. For example, the models 140 can be or can otherwise include various machine-learned models. Example machine-learned models include neural networks or other multi-layer non-linear models. Example neural networks include feed forward neural networks, deep neural networks, recurrent neural networks, and convolutional neural networks. Example models 140 are discussed with reference to FIG. 2.

The user computing device 102 and/or the server computing system 130 can train the models 120 and/or 140 via interaction with the training computing system 150 that is communicatively coupled over the network 180. The training computing system 150 can be separate from the server computing system 130 or can be a portion of the server computing system 130.

The training computing system 150 includes one or more processors 152 and a memory 154. The one or more processors 152 can be any suitable processing device (e.g., a processor core, a microprocessor, an ASIC, a FPGA, a controller, a microcontroller, etc.) and can be one processor or a plurality of processors that are operatively connected. The memory 154 can include one or more non-transitory computer-readable storage mediums, such as RAM, ROM, EEPROM, EPROM, flash memory devices, magnetic disks, etc., and combinations thereof. The memory 154 can store data 156 and instructions 158 which are executed by the processor 152 to cause the training computing system 150 to perform operations. In some implementations, the training computing system 150 includes or is otherwise implemented by one or more server computing devices.

The training computing system 150 can include a model trainer 160 that trains the machine-learned models 120 and/or 140 stored at the user computing device 102 and/or the server computing system 130 using various training or learning techniques, such as, for example, backwards propagation of errors. For example, a loss function can be back-propagated through the model(s) to update one or more parameters of the model(s) (e.g., based on a gradient of the loss function). Various loss functions can be used such as mean squared error, likelihood loss, cross entropy loss, hinge loss, and/or various other loss functions. Gradient descent techniques can be used to iteratively update the parameters over a number of training iterations.

In some implementations, performing backwards propagation of errors can include performing truncated back-propagation through time. The model trainer 160 can perform a number of generalization techniques (e.g., weight decays, dropouts, etc.) to improve the generalization capability of the models being trained.

In particular, the model trainer 160 can train the joint prediction models 120 and/or 140 based on a set of training data 162. The training data 162 can include, for example, historical time-series data comprising a plurality of historical observations and historical interventions. Additionally, the training data 162 can include historical event data. For example, the training data 162 can include a plurality of historical patient records each comprising a plurality of historical clinical measurements and/or historical clinical interventions. As another example, the training data 162 can include temporal data related to an event of interest, such as the occurrence of a mortality event or death.

In some implementations, if the user has provided consent, the training examples can be provided by the user computing device 102. Thus, in such implementations, the model 120 provided to the user computing device 102 can be trained by the training computing system 150 on user-specific data received from the user computing device 102. In some instances, this process can be referred to as personalizing the model.

The model trainer 160 includes computer logic utilized to provide desired functionality. The model trainer 160 can be implemented in hardware, firmware, and/or software controlling a general purpose processor. For example, in some implementations, the model trainer 160 includes program files stored on a storage device, loaded into a memory and executed by one or more processors. In other implementations, the model trainer 160 includes one or more sets of computer-executable instructions that are stored in a tangible computer-readable storage medium such as RAM hard disk or optical or magnetic media.

The network 180 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

FIG. 1A illustrates one example computing system that can be used to implement the present disclosure. Other computing systems can be used as well. For example, in some implementations, the user computing device 102 can include the model trainer 160 and the training dataset 162. In such implementations, the models 120 can be both trained and used locally at the user computing device 102. In some of such implementations, the user computing device 102 can implement the model trainer 160 to personalize the models 120 based on user-specific data.

FIG. 1B depicts a block diagram of an example computing device 10 that performs according to example embodiments of the present disclosure. The computing device 10 can be a user computing device or a server computing device.

The computing device 10 includes a number of applications (e.g., applications 1 through N). Each application contains its own machine learning library and machine-learned model(s). For example, each application can include a machine-learned model. Example applications include a text messaging application, an email application, a dictation application, a virtual keyboard application, a browser application, etc.

As illustrated in FIG. 1B, each application can communicate with a number of other components of the computing device, such as, for example, one or more sensors, a context manager, a device state component, and/or additional components. In some implementations, each application can communicate with each device component using an API (e.g., a public API). In some implementations, the API used by each application is specific to that application.

FIG. 1C depicts a block diagram of an example computing device 50 that performs joint prediction according to example embodiments of the present disclosure. The computing device 50 can be a user computing device or a server computing device.

The computing device 50 includes a number of applications (e.g., applications 1 through N). Each application is in communication with a central intelligence layer. Example applications include a text messaging application, an email application, a dictation application, a virtual keyboard application, a browser application, etc. In some implementations, each application can communicate with the central intelligence layer (and model(s) stored therein) using an API (e.g., a common API across all applications).

The central intelligence layer includes a number of machine-learned models. For example, as illustrated in FIG. 1C, a respective machine-learned model (e.g., a model) can be provided for each application and managed by the central intelligence layer. In other implementations, two or more applications can share a single machine-learned model. For example, in some implementations, the central intelligence layer can provide a single model (e.g., a single model) for all of the applications. In some implementations, the central intelligence layer is included within or otherwise implemented by an operating system of the computing device 50.

The central intelligence layer can communicate with a central device data layer. The central device data layer can be a centralized repository of data for the computing device 50. As illustrated in FIG. 1C, the central device data layer can communicate with a number of other components of the computing device, such as, for example, one or more sensors, a context manager, a device state component, and/or additional components. In some implementations, the central device data layer can communicate with each device component using an API (e.g., a private API).

EXAMPLE METHODS

Figure 4:
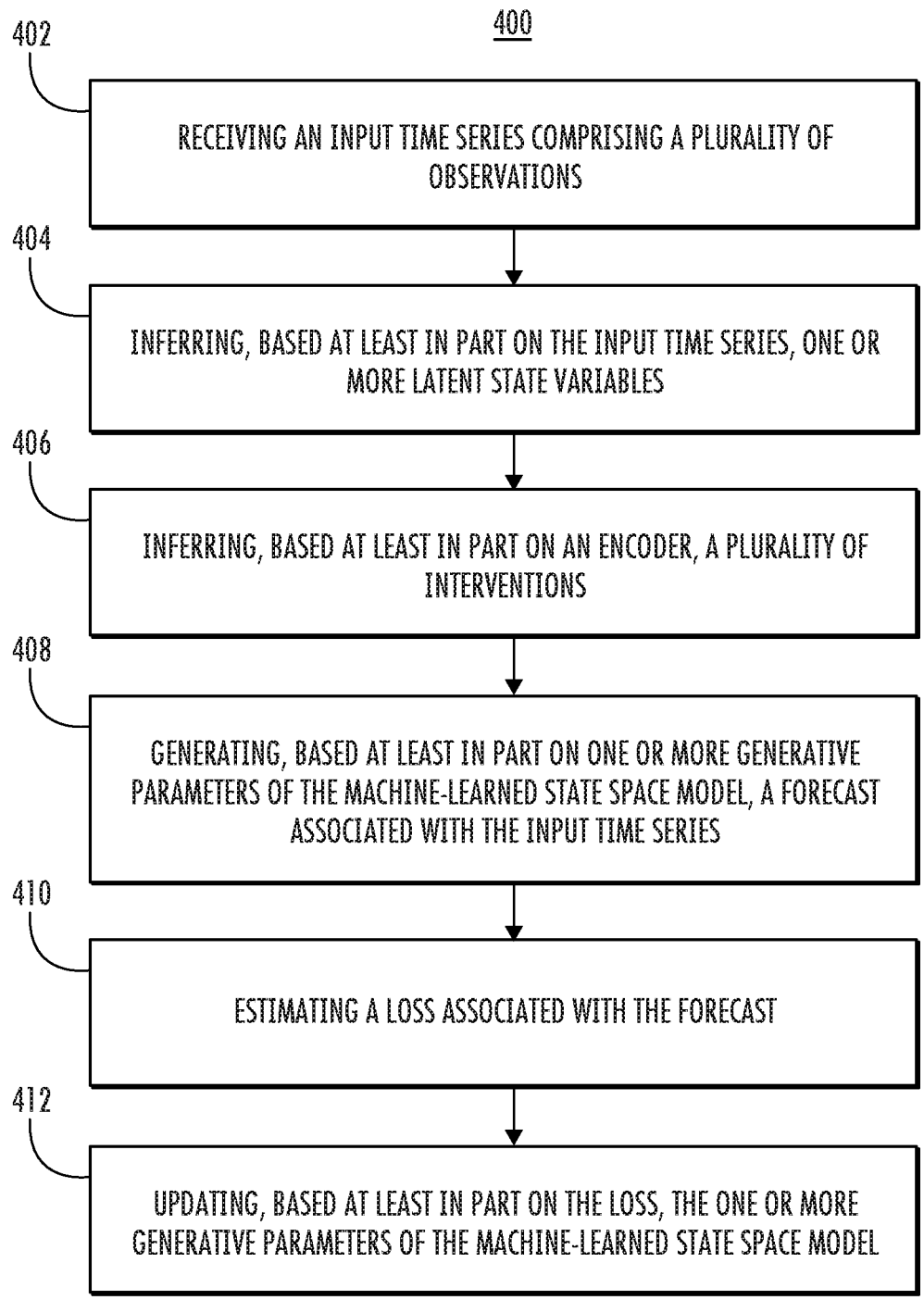
FIG. 4 depicts a flow chart diagram of an example method to perform joint prediction according to example embodiments of the present disclosure.

FIG. 4 depicts a flow chart diagram of an example method 400 to perform joint prediction according to example embodiments of the present disclosure. Although FIG. 4 depicts steps performed in a particular order for purposes of illustration and discussion, the methods of the present disclosure are not limited to the particularly illustrated order or arrangement. The various steps of the method 400 can be omitted, rearranged, combined, and/or adapted in various ways without deviating from the scope of the present disclosure.

At 402, a computing system can receive one or more input time series including a plurality of observations and/or a plurality of interventions. For example, the plurality of observations can comprise clinical observations collected over a series of time. For example, the plurality of observations can have one or more dimensions, each dimension corresponding to a different type or modality of clinical measurement. In some embodiments, the input time series can be extracted from one or more electronic medical records associated with a patient. For example, the plurality of observations of the system can be or can include a plurality of clinical measurements of the patient. Additionally and/or alternatively, the plurality of interventions performed on the system comprise a plurality of clinical interventions performed on the patient. The time series can include de-identified data, such as data including no protected health information.

At 404, the computing system can infer, based at least in part on the input time series, one or more latent state variables. At 406, the computing system can infer, based at least in part on an encoder, a plurality of interventions. For example, the computing system can generate, based at least in part on the encoder, a probability distribution approximating a posterior associated with the one or more latent state variables, the plurality of observations, and the plurality of interventions; and maximize a likelihood associated with the probability distribution by minimizing a lower bound associated with a loss of the probability distribution.

At 408, the computing system can generate, based at least in part on one or more generative parameters of the machine-learned state space model, a forecast associated with the input time series. For example, the one or more generative parameters can be associated with at least the encoder. For example, the forecast can be generated by maximizing a joint likelihood associated with a forecasted plurality of observations and a forecasted plurality of interventions based at least in part on the input time series. For instance, the joint likelihood can be maximized by minimizing a forecast loss associated with the forecasted plurality of observations and the forecasted plurality of interventions and a regularization loss associated with the one or more latent state variables. As another example, the forecast associated with the input time series can comprise a time-to-event prediction, and generating the forecast associated with the input time series can comprise estimating a log likelihood associated with an event as a function of time.

At 410, the computing system can estimate a loss associated with the forecast. For instance, the loss of the probability distribution can comprise a reconstruction loss associated with the plurality of observations and the plurality of interventions and a regularization loss between the probability distribution and a prior distribution of the one or more latent state variables.

At 412, the computing system can update, based at least in part on the loss, the one or more generative parameters of the machine-learned state space model. For example, the one or more generative parameters can be adjusted according to a gradient defined by the loss. For example, the one or more generative parameters can be adjusted in a negative direction with respect to the gradient.

ADDITIONAL DISCLOSURE

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computing system configured for joint prediction of future time-series and time-to-event, the computing system comprising:
   one or more processors; and
   one or more non-transitory computer-readable media that collectively store:
      a machine-learned state space model comprising at least a first machine-learned function that models a relationship between a past state of the machine-learned state space model and a likelihood of a future intervention associated with the machine-learned state space model and a second machine-learned function that models an effect of a past intervention on a future state of the machine-learned state space model, the machine-learned state space model configured to:
         receive one or more input time series;
         input, responsive to the receiving and based at least in part on the one or more input time series, to the first machine-learned function, data indicative of one or more states of the system at a first time associated with the one or more input time series;
         subsequently receive, from the first machine-learned function based on the data indicative of the one or more states, data indicative of one or more probabilities that one or more future interventions will be performed on the system at a second time later than the first time;
         input, responsive to the receiving, to the second machine-learned function of the machine-learned state space model, the data indicative of the one or more probabilities that the one or more future interventions will be performed on the system at the second time;
         subsequently receive, from the second machine-learned function based on the data indicative of the one or more probabilities that the one or more future interventions will be performed on the system at the second time, data indicative of one or more predicted states of the system at one or more third times later than the second time; and
         output, based at least in part on the data indicative of the one or more predicted states, one or more trajectory predictions and a time-to-event prediction, wherein the one or more trajectory predictions comprise a future time series for one or both of future observations of the system or future interventions performed on the system; and
      instructions that, when executed by the one or more processors, cause the computing system to perform operations, the operations comprising:
         inputting the one or more input time series into the machine-learned state space model; and
         receiving the one or more trajectory predictions and the time-to-event prediction as an output of the machine-learned state space model.

2. The computing system of claim 1, wherein:
   the one or more input time series are extracted from one or more electronic medical records associated with a patient;
   the one or more input time series comprise a plurality of clinical measurements of the patient; and
   the one or more input time series comprise a plurality of clinical interventions performed on the patient.

3. The computing system of claim 1, wherein an event associated with the time-to-event prediction comprises at least one of a mortality event or onset of acute condition.

4. The computing system of claim 1, wherein the time-to-event prediction output by the machine-learned state space model comprises a hazard series defined at one or more points in time associated with the one or more trajectory predictions.

5. The computing system of claim 4, wherein the operations further comprise determining a survival function based at least in part on the hazard series.

6. The computing system of claim 1, wherein the machine-learned state space model is a non-linear state space model that comprises one or more neural networks.

7. The computing system of claim 6, wherein the one or more neural networks comprise one or more multilayer perceptron networks that model state transition, observation, and emission rate functions.

8. The computing system of claim 1, wherein the operations further comprise a pretraining step, wherein the pretraining step comprises:
identifying one or more generative parameters associated with the machine-learned state space model, the one or more generative parameters identified by variational inference of a variational distribution that approximates a probability distribution associated with the one or more generative parameters;
generating, based at least in part on the one or more generative parameters, a training data set; and
adjusting the one or more generative parameters based at least in part on a loss associated with the training data set.

9. The computing system of claim 8, wherein the variational distribution is generated using an encoder.

10. The computing system of claim 1, wherein an intervention associated with a first point in the one or more input time series is related to a state variable associated with a second point in the input time series via a transform equation.

11. The computing system of claim 1, wherein a state transition associated with the machine-learned state space model is modeled by a probability distribution and wherein a variance of the probability distribution is modeled by a process and measurement noise covariance matrix.

12. The computing system of claim 1, wherein the machine-learned state space model further comprises:
a third machine-learned function that models a relationship between a state of a machine learned model and a future state of the machine-learned model without external influence;
a fourth machine-learned function that models a relationship between the state of the machine-learned state space model and an observation; and
a fifth machine-learned function that models a relationship between the state of the machine-learned state space model and a hazard rate.

13. A computer-implemented method of training a machine-learned state space model, the computer-implemented method comprising:
receiving, by one or more computing devices, an input time series comprising a plurality of observations;
inferring, by the one or more computing devices and based at least in part on the input time series, one or more first latent state variables associated with one or more first times of the input time series;
inferring, by the one or more computing devices and based at least in part on an encoder and based at least in part on the one or more first latent state variables, a plurality of probabilities of a plurality of interventions at one or more second times later than the one or more first times;
inferring, by the one or more computing devices and based at least in part on the plurality of probabilities, one or more second latent state variables associated with one or more third times later than the one or more second times;
generating, by the one or more computing devices and based at least in part on one or more generative parameters of the machine-learned state space model and based at least in part on the one or more second latent state variables, a forecast associated with the input time series;
estimating, by the one or more computing devices, a loss associated with the forecast; and
updating, by the one or more computing devices and based at least in part on the loss, the one or more generative parameters of the machine-learned state space model.

14. The method of claim 13, wherein inferring the one or more latent state variables and inferring the plurality of probabilities of the plurality of interventions comprises:
generating, based at least in part on the encoder, a probability distribution approximating a posterior associated with the one or more latent state variables, the plurality of observations, and the plurality of interventions; and
maximizing a likelihood associated with the probability distribution by minimizing a lower bound associated with a loss of the probability distribution.

15. The method of claim 14, wherein the loss of the probability distribution comprises a reconstruction loss associated with the plurality of observations and the plurality of interventions and a regularization loss between the probability distribution and a prior distribution of the one or more latent state variables.

16. The method of claim 13, wherein generating the forecast associated with the input time series comprises maximizing a joint likelihood associated with a forecasted plurality of observations and a forecasted plurality of interventions based at least in part on the input time series.

17. The method of claim 16, wherein the joint likelihood is maximized by minimizing a forecast loss associated with the forecasted plurality of observations and the forecasted plurality of interventions and a regularization loss associated with the one or more latent state variables.

18. The method of claim 13, wherein the forecast associated with the input time series comprises a time-to-event prediction, wherein generating the forecast associated with the input time series comprises estimating a log likelihood associated with an event as a function of time.

19. The method of claim 13, wherein the state space model is a non-linear state space model utilizing one or more neural networks.

20. The method of claim 13, wherein the input time series comprises electronic medical record data, wherein the plurality of observations comprises a plurality of clinical measurements, wherein the plurality of interventions comprises a plurality of clinical interventions, and wherein one or more latent state variables associated with the machine-learned state space model are associated with a latent health state of a patient.

* * * * *